United States Patent
Ballard et al.

(10) Patent No.: US 6,863,852 B1
(45) Date of Patent: Mar. 8, 2005

(54) FLUOROPOLYMER EXTRUSIONS BASED ON NOVEL COMBINATIONS OF PROCESS PARAMETERS AND CLAY MINERALS

(75) Inventors: Robert L. Ballard, Orangeburg, SC (US); Eric R. George, Orangeburg, SC (US)

(73) Assignee: Zeus Industrial Products, Inc., Orangeburg, SC (US)

( * ) Notice: Subject to any disclaimer, the term of this patent is extended or adjusted under 35 U.S.C. 154(b) by 128 days.

(21) Appl. No.: 10/447,253

(22) Filed: May 28, 2003

Related U.S. Application Data

(60) Provisional application No. 60/400,239, filed on May 30, 2002, and provisional application No. 60/385,709, filed on May 30, 2002.

(51) Int. Cl.$^7$ .......................... B32B 31/00; D04H 1/16; B29C 59/00; B27J 5/00
(52) U.S. Cl. ...................... 264/112; 264/113; 264/119; 264/122; 264/127; 156/294
(58) Field of Search ................. 264/112, 113, 264/119, 122, 127; 156/294

(56) References Cited

U.S. PATENT DOCUMENTS

| | | | |
|---|---|---|---|
| 4,472,538 A | | 9/1984 | Kamigaito et al. |
| 4,810,734 A | | 3/1989 | Kawasumi et al. |
| 5,068,289 A | | 11/1991 | George et al. |
| 5,385,776 A | | 1/1995 | Maxfield et al. |
| 5,433,909 A | * | 7/1995 | Martakos et al. ........ 264/209.1 |
| 5,552,100 A | * | 9/1996 | Shannon et al. ............ 264/127 |
| 5,554,120 A | | 9/1996 | Chen et al. |
| 5,556,383 A | | 9/1996 | Wang et al. |
| 5,565,523 A | | 10/1996 | Chen et al. |
| 5,578,672 A | | 11/1996 | Beall et al. |
| 5,698,624 A | | 12/1997 | Beall et al. |
| 5,726,247 A | | 3/1998 | Michalczyk et al. |
| 5,747,560 A | | 5/1998 | Christiani et al. |
| 5,747,591 A | | 5/1998 | Chen et al. |
| 5,830,182 A | | 11/1998 | Wang et al. |
| 5,877,248 A | | 3/1999 | Beall et al. |
| 5,880,197 A | | 3/1999 | Beall et al. |
| 5,951,941 A | | 9/1999 | Wang et al. |
| 5,980,799 A | * | 11/1999 | Martakos et al. ........... 264/127 |
| 6,010,521 A | | 1/2000 | Lee et al. |
| 6,013,728 A | | 1/2000 | Chen et al. |
| 6,060,549 A | | 5/2000 | Li et al. |
| 6,192,942 B1 | | 2/2001 | Hsich et al. |
| 6,200,290 B1 | | 3/2001 | Burgmeier |
| 6,210,396 B1 | | 4/2001 | MacDonald et al. |
| 6,217,547 B1 | | 4/2001 | Lee |
| 6,271,297 B1 | | 8/2001 | Ishida |
| 6,271,298 B1 | | 8/2001 | Powell |

(List continued on next page.)

OTHER PUBLICATIONS

US 6,362,268, 3/2002, Bishop et al. (withdrawn)

Primary Examiner—Stephen J. Lechert, Jr.
(74) Attorney, Agent, or Firm—Sperry, Zoda & Kane

(57) ABSTRACT

A process for extruding of products from fluoropolymers preferably shaped as rods or tubes which have unique physical and other properties resulting from the addition of nanoparticles under unique processing conditions while also utilizing accurate control of processing parameters such as time and temperature and others according to novel methods.

56 Claims, 4 Drawing Sheets

U.S. PATENT DOCUMENTS

| | | |
|---|---|---|
| 6,287,992 B1 | 9/2001 | Polansky et al. |
| 6,339,121 B1 | 1/2002 | Rafailovich et al. |
| 6,341,747 B1 | 1/2002 | Schmidt et al. |
| 6,344,271 B1 | 2/2002 | Yadav et al. |
| 6,350,805 B1 | 2/2002 | Korbee et al. |
| 6,368,586 B1 | 4/2002 | Jacob et al. |
| 6,395,208 B1 * | 5/2002 | Herweck et al. ............ 264/127 |
| 2001/0011109 A1 | 8/2001 | Tomalia et al. |
| 2001/0025076 A1 | 9/2001 | Lan et al. |
| 2001/0033924 A1 | 10/2001 | Qian et al. |
| 2001/0056149 A1 | 12/2001 | Powell |
| 2002/0004136 A1 | 1/2002 | Gao et al. |
| 2002/0010248 A1 | 1/2002 | Fompevie et al. |
| 2002/0012675 A1 | 1/2002 | Jain et al. |
| 2002/0012806 A1 | 1/2002 | Flepp et al. |
| 2002/0014182 A1 | 2/2002 | Yadav et al. |
| 2002/0022672 A1 | 2/2002 | Thunhorst et al. |
| 2002/0024171 A1 | 2/2002 | Rohde et al. |
| 2002/0028288 A1 | 3/2002 | Rohrbaugh et al. |
| 2002/0032272 A1 | 3/2002 | Sievens et al. |

* cited by examiner

Figure 1. PTFE/Clay Data Sheet

| Property | Test Method | Units | 0.0015 Max Wall Virgin PTFE | 0.001 Wall (3% Nanoparticles) | 0.0007 Wall (3% Nanoparticles) |
|---|---|---|---|---|---|
| Tensile Strength | ASTM D638 | psi | 11,000 | 23,000 | 14,000 |
| Tensile Modulus | ASTM D638 | psi | 250,000 | 500,000 | 500,000 |
| Elongation @ Break | ASTM D638 | % | 300 | 180 | 120 |
| Burst Pressure | ASTM D1599 | lb | 67 | 74 | 34 |
| Contact Angle w/o etch | ML 46628 | deg | >90 | 99 | 99 |
| Contact Angle w/ etch | ML 46628 | deg | 54 | 64 | 64 |
| Class VI Approval | USP 24 | | Yes | Yes | Yes |
| Pinholes | | amp | 0 | 0 | 0 |
| Sampling | | | 2 Part samples | 4 Vertical runs | 5 Horizontal, 3 Vertical |
| Wall Average | | inch | 0.00095 | 0.00096 | 0.00068 |
| ID Average | | inch | 0.0698 | 0.06525 | 0.0705 |
| Wall 99% Confidence | | | 0.00089–0.00101 | 0.00089–0.00102 | 0.00066–0.00069 |
| Wall Prob > 75% | | | $0.00095 \pm 0.0002$ | $0.00095 \pm 0.0002$ | $0.0007 \pm 0.0002$ |
| ID 99% Confidence | | | 0.0695–0.0700 | 0.0648–0.0657 | 0.0704–0.0708 |
| ID Prob > 75% | | | $0.069 \pm 0.001$ | $0.065 \pm 0.001$ | $0.071 \pm 0.001$ |
| ID Prob > 75% | | | $0.069 \pm 0.001$ | $0.065 \pm 0.001$ | $0.071 \pm 0.001$ |
| Coefficient of Friction | Dynamic | | | | |

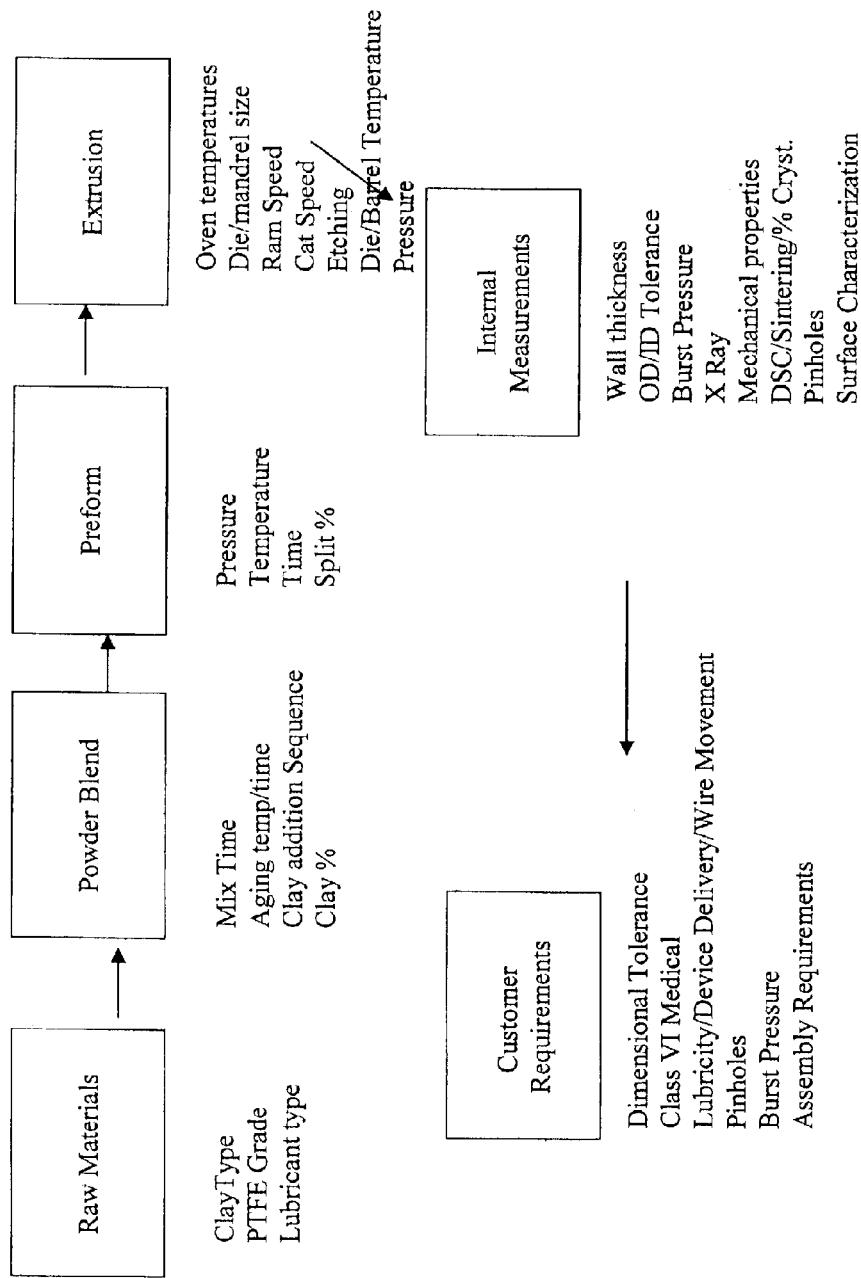
Figure 2      PTFE Nanocomposite Flow Chart

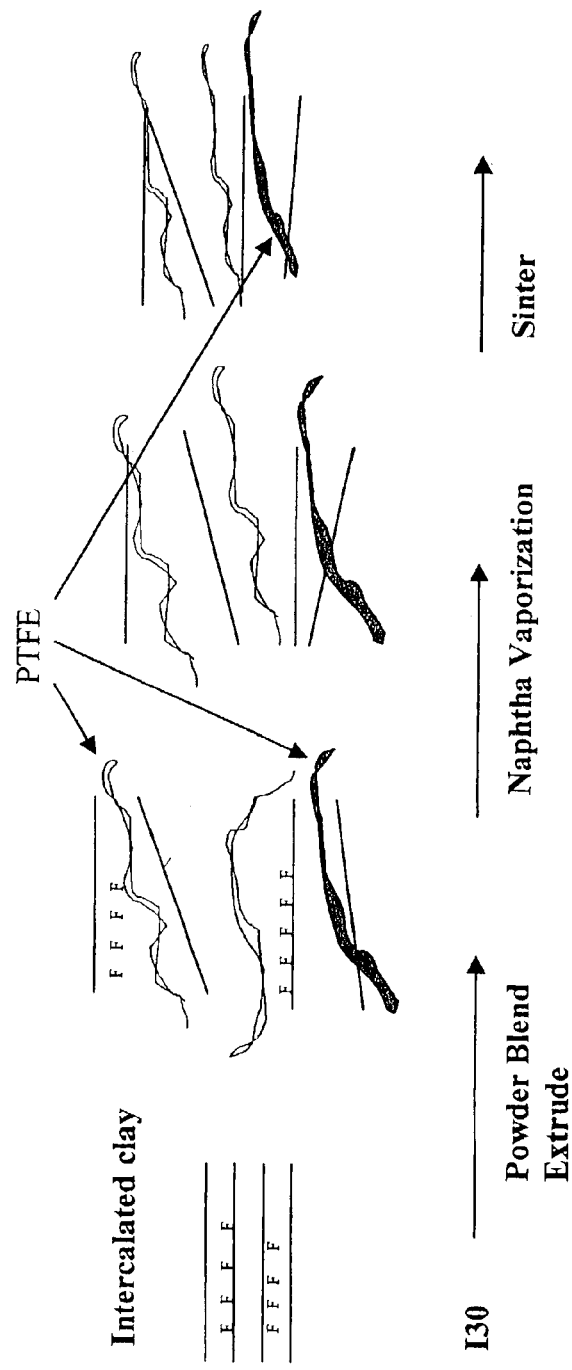

Figure 4    Current Process PTFE/Clay Intercalation
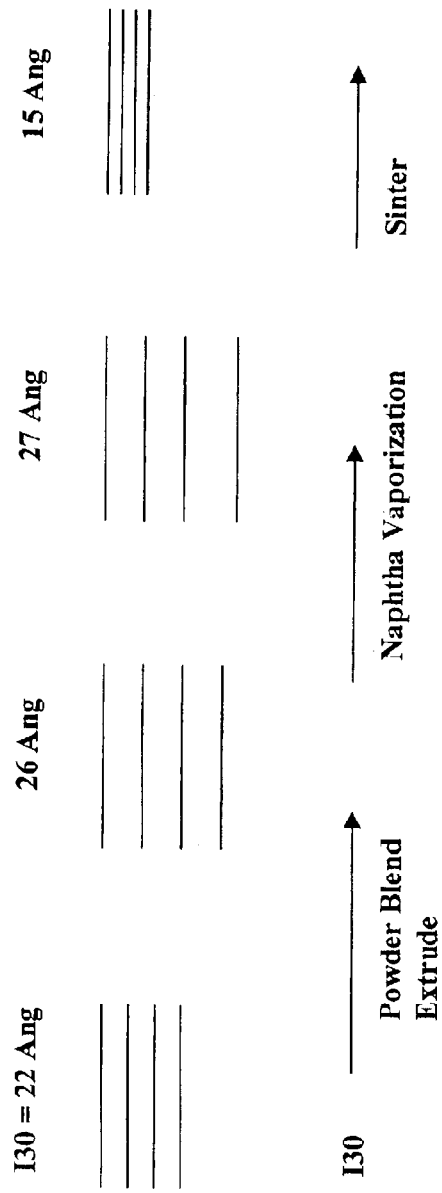
The Powder Blend, Preform, Naphtha Vaporization Steps Expand the Clay Layers Followed By a collapse of the layers in the Sintering Step. The Results Were Identical for Clay Added in Naphtha Versus in the Powder.

FLUOROPOLYMER EXTRUSIONS BASED ON NOVEL COMBINATIONS OF PROCESS PARAMETERS AND CLAY MINERALS

This patent application claims priority based on U.S. provisional patent application No. 60/400,239 filed May 30, 2002 on IMPROVED FLUOROPOLYMER EXTRUSIONS BASED ON NOVEL CONBINATIONS OF PROCESS PARAMETERS AND CLAY MINERALS and on U.S. Provisional Patent application No. 60/385,709 filed May 30, 2002 on IMPROVED FLUOROPOLYNER EXTRUSIONS BASED ON NOVEL COMBINATIONS OF PROCESS PARAMETERS AND CLAY MINERALS, both filed by the inventors, Robert L. Ballard and Eric R. George and assigned to Zeus Industrial Products, Inc.

ABSTRACT OF THE INVENTION

A process for extruding of products from fluoropolymers preferably shaped as rods or tubes which have unique physical and other properties resulting from the addition of nanoparticles under unique processing conditions while also utilizing accurate control of processing parameters such as time and temperature and others according to novel methods.

BACKGROUND OF THE INVENTION

1. Field of Invention

The present invention deals with the formation of enhanced fluoropolymer extrusions made possible by unique modifications to the processing parameters and the novel introduction of various clay minerals not previously contemplated. The advancement set forth by the present invention and the preferred embodiment disclosed herein is related to fluoropolymer filled and reinforced systems formed under novel processing conditions for combination with intercalated clay minerals to produce composites that exhibit a unique set of physical properties. These physical properties present a uniquely possible balance not possible heretofore.

2. Description of the Prior Art

The present invention deals with the analysis of the mechanical and other properties of polymer composites and polymer blends and, in particular, such polymers and polymer blends which are reinforced by an added component. Numerous patents have been granted in this field particularly including the use of nanoparticles for strengthening polymers and copolymers and the use of polymer blends such as shown in U.S. Pat. No. 4,472,538 patented Sep. 18, 1984 to 0. Kamigaito et al and assigned to Kabushiki Kaisha Toyota Chuo Kenkyusho on a "Composite Material Composed Of Clay Mineral And Organic High Polymer And Method For Producing The Same"; and U.S. Pat. No. 4,810,734 patented Mar. 7, 1989 to M. Kawasumi et al and assigned to Kabushiki Kaisha Toyota Chuo Kenkyusho on a "Process For Producing Composite Material"; and U.S. Pat. No. 5,068,289 patented Nov. 26, 1991 to E. George et al and assigned to Shell Oil Company on a "Reinforced Polymer Compositions"; and U.S. Pat. No. 5,385,776 patented Jan. 31, 1995 to M. Maxfield et al and assigned to AlliedSignal Inc. on "Nanocomposites Of Gamma Phase Polymers Containing Inorganic Particulate Material"; and U.S. Pat. No. 5,554,120 patented Sep. 10, 1996 to Z. Chen et al and assigned to Advanced Cardiovascular Systems, Inc. on "Polymer Blends For Use In Making Medical Devices Including Catheters And Balloons For Dilatation Catheters"; and U.S. Pat. No. 5,556,383 patented Sep. 17, 1996 to L. Wang et al and assigned to Scimed Lifesystems, Inc. on "Block Copolymer Elastomer Catheter Balloons"; and U.S. Pat. No. 5,565,523 patented Oct. 15, 1996 to Z. Chen et al and assigned to Advanced Cardiovascular Systems, Inc. on "Polymer Blends For Use In Making Medical Devices Including Catheters And Balloons For Dilatation Catheters"; and U.S. Pat. No. 5,578,672 patented Nov. 26, 1996 to G. Beall et al and assigned to Ancol International Corporation on an "Intercalates; Exfoliates; Process For Manufacturing Intercalates And Exfoliates And Composite Materials Containing Same"; and U.S. Pat. No. 5,698,624 patented Dec. 16, 1997 to G. Beall et al and assigned to AMCOL International Corporation on an "Exfoliated Layered Materials And Nanocomposites Comprising Matrix Polymers And Said Exfoliated Layered Materials Formed With Water Insoluble Oligomers And Polymers"; and U.S. Pat. No. 5,726,247 patented Mar. 10, 1998 to M. Michalczyk et al and assigned to E. I Du Pont de Nemours and Company on "Fluoropolymer Nanocomposites"; and U.S. Pat. No. 5,747, 560 patented May 5, 1998 to B. Christiani et al and assigned to Allied Signal Inc. on a "Melt Process Formation of Polymer Nanocomposite Of Exfoliated Layered Material"; and U.S. Pat. No. 5,747,591 patented May 5, 1998 to Z. Chen et al and assigned to Advanced Cardiovascular Systems, Inc. on "Polymer blends For Use In Making Medical Devices Including Catheters And Balloons For Dilation Catheters"; and U.S. Pat. No. 5,830,182 patented Nov. 3, 1998 to L. Wang et al and assigned to Scimed Life Systems, Inc. on "Block Copolymer Elastomer Catheter Balloons"; and U.S. Pat. No. 5,877,248 patented Mar. 2, 1999 to G. Beall et al and assigned to AMCOL International Corporation on "Intercalates And Exfoliates Formed With Oligomers And Polymers And Composite Materials Containing Same"; and U.S. Pat. No. 5,880,197 patented Mar. 9, 1999 to G. Beall et al and assigned to AMCOL International Corporation on "Intercalates And Exfoliates Formed With Monomeric Amines And Amides; Composite Materials Containing Same And Methods Of Modifying Rheology Therewith"; and U.S. Pat. No. 5,951,941 patented Sep. 14, 1999 to L. Wang et al and assigned to Scimed Life Systems, Inc. on "Block Copolymer Elastomer Catheter Balloons"; and U.S. Pat. No. 6,010,521 patented Jan. 4, 2000 to J. Lee et al and assigned to Advanced Cardiovascular Systems, Inc. on a "Catheter Member With Bondable Layer"; and U.S. Pat. No. 6,013,728 patented Jan. 11, 2000 to Z. Chen et al and assigned to Advanced Cardiovascular Systems, Inc. on "Polymer Blends For Use In Making Medical Devices Including Catheters And Balloons For Dilatation Catheters"; and U.S. Pat. No. 6,060,549 patented May 9, 2000 to D. Li et al and assigned to Exxon Chemical Patents, Inc. on "Rubber Toughened Thermoplastic Resin Nano Composites"; and U.S. Pat. No. 6,192,942 patented Feb. 27, 2001 to H. S. Hsich et al and assigned to Hybritech Polymers on a "Multi Layer Tubing Assembly For Fluid And Vapor Handling Systems"; and U.S. Pat. No. 6,200,290 patented Mar. 13, 2001 to R. Burgmeier and assigned to Schneider (USA) Inc. on "Dilatation Balloons Containing Polyesteretheramide Copolymer"; and U.S. Pat. No. 6,210,396 patented Apr. 3, 2001 to S. MacDonald et al and assigned to Medtronic, Inc. on a "Guiding Catheter With Tungsten Loaded Band"; and U.S. Pat. No. 6,217,547 patented Apr. 17, 2001 to J. Lee and assigned to Advanced Cardiovascular Systems, Inc. on a "Lubricous And Readily Bondable Catheter Shaft"; and U.S. Pat. No. 6,271,297 patented Aug. 7, 2001 to H. Ishida and assigned to Case Western Reserve University on a "General Approach To Nanocomposite Preparation"; and U.S. Pat. No. 6,271,298 patented Aug. 7, 2001 to C. Powell and assigned to Southern Clay Products, Inc. on a "Process For Treating Smectite Clays To Facilitate Exfoliation"; and U.S. Pat. No. 6,287,992 to C. Polansky et al and assigned to The Dow Chemical Company on a "Polymer Composite And A Method For Its Preparation"; and U.S. Pat. No. 6,339,121 patented Jan. 15, 2002 to M. Rafailovich et al and assigned to The Research Foundation at State University of New York on a "Compatibilizer For Immiscible olymer Blends"; and U.S. Pat. No. 6,341,747 patented Jan. 29, 2002 to W. Schmidt et al and assigned to United Technologies Corporation on a "Nanocomposite Layered Airfoil"; and U.S. Pat. No. 6,344,271 patented Feb. 5, 2002 to T. Yadav et al and assigned to NanoEnergy Corporation on "Materials And Products Using Nanostructured Non-Stoichimetric Substances"; and U.S. Pat. No. 6,350,805 patented Feb. 26, 2002 to R. Korbee et al and assigned to DSM N.V. on a "Process For The Preparation Of A Polyamide Nanocomposite Composition"; and U.S. Pat. No. 6,362,268 patented Mar. 26, 2002 to C. Bishop et al and assigned to Montell Technology Company BV on an "Intercalated Clay Useful For Making An Olefin Polymer Material Nanocomposite"; and U.S. Pat. No. 6,368,586 patented Apr. 9, 2002 to J. Jacob et al and assigned to Brown University Research Foundation on "Methods And Compositions For Enhancing The Bioadhesive Properties Of Polymers"; and U.S. Pat. Publication No. US2001/0011109 published Aug. 2, 2001 to D. Tomalia on "Nanocomposites Of Dendritic Polymers"; and Unitet states Publication No. US2001/D025076 published Sep. 27, 2001 to T. Lan et al on "Layered Compositions With Multi-Charged Onium Ions As Exchange Cations, And Their Application To Prepare Monomer, Oligomer, And Polymer Intercalates And Nanocomposites Prepared With The Layered Compositions Of The Intercalates"; and United Stated Publication No. US2001/0033924 published Oct. 25, 2001 to G. Qian et al on "Intercalates Formed With Polypropylene/Maleic Anhydride-Modified Polypropylene Intercalants"; and U.S. Pat. Publication No. US2001/0056149 published Dec. 27, 2001 to C. Powell on a "Process For Treating Smectite Clays To Facilitate Exfoliation"; and United States Publication No. US2002/0004136 published Jan. 10, 2002 to Y. Gao et al on "CarbonNanotubes On A Substrate"; and United Stated Publication No. US2002/0010248 published Jan. 24, 2002 to L. Fomperie et al on a "Nanocomposite Based On A Bridged Clay, And Cable Comprising Said Composite"; and United States Publication No. US2C02/0012675 published Jan. 31, 2002 to R. Jain et al on "Controlled Release Nanoparticulate Compositions"; and United States Publication No. US2002/0012806 published Jan. 31, 2002 to A. Flepp et al on "Thermoplastic Multilayer Composites"; and United States Publication No. US2002/0014182 published Feb. 7, 2002 to T. Yadav et al on "Nanostructured Fillers And Carriers"; and United States Publication No. US2002/0022672 published Feb. 21, 2002 to K. Thunhorst et al on "Foams Containing Functionalized Metal Oxide Nanoparticles And Methods Of Making Same"; and United States Publication No. US2002/0024171 published Feb. 28, 2002 to W. Rohde et al on "Production Of Hollow Plastic Articles"; and Unites States Patent Publication No. US2002/0028288 published Mar. 7, 2002 to R. Rohrbaugh et al on "Long Lasting Coatings For Modifying Hard Surfaces And Processes For Applying The Same"; and United States Publication No. US2002/0032272 published Mar. 14, 2002 to W. Sievers et al on "Nanoporous Interpenetrating Organic/Inorganic Networks".

SUMMARY OF THE INVENTION

The present invention as disclosed herein includes tetrafluoroethylene homopolymers, its copolymers, and terpolymers with hexafluoropropylene, vinylidene fluoride, perfluorovinylethers, vinyl fluoride, and ethylene. This invention is applicable to a range of materials far broader than described above, however, these disclosed materials comprise the primary areas of utility at this time.

These polymers, copolymers, and terpolymers are commonly referred to as PTFE, FEP, THV, ETFE, PFA, PVF and PVDF. The preferred examples of this inventive concept are based on PTFE, poly(tetrafluoroethylene) and FEP (a copolymer of PTFE with hexafluoropropylene). The scope of the present invention extends to several aspects of PCTA (Percutaneous Transluminal Coronary Angioplasty) that include novel designs for guide catheters, balloon catheters, and any tube requiring a novel balance of lubricity, mechanical properties and thin wall capabilities. The scope of this invention can also extend to the production of fusion rods utilized in the manufacture of catheters. This concept can also extend to industrial applications for diagnostic equipment, wiring conduits as well as wire coatings, generally.

A key advantage of this unique combination is in the capability of use with the ram extrusion (paste extrusion) of PTFE and the melt extrusion of FEP. Paste extrusion is a processing method for PTFE since PTFE homopolymers of high molecular weight are not capable of melt processing by traditional plastic processing methods. The present invention also offers benefits for tubing commonly referred to as "layflat" tubing where the extruded product is processed in the form of collapsed tubing onto rolls. This "layflat" tubing can be used in medical procedures, and for packaging of medical and semiconductor components. We have demonstrated with FEP that a novel electrostatic dissipation effect occurs upon the introduction of nanoparticles not seen in the virgin layflat material.

An important aspect of the present invention involves the use of PTFE for heat shrink tubing capable of higher expansions and shrink back ratios than is currently possible in the current state of the art.

The reference book entitled "Fluoroplastics, Vol. 1, Non-Melt Processible Fluoroplastics" (2000) summarizes all the key aspects of PTFE technology and paste extrusion of those skilled in the art. It also has a widely read section on filled Fluoropolymer compounds. PTFE materials are grouped into three categories of namely, PTFE dispersions, granular (suspension polymerized) and fine powder (dispersion polymerized). While all of the examples set forth herein for PTFE are based on fine powder ram extrusion, it has been contemplated heretofore to apply these same principles to ram extrusion of granular PTFE with some possibility of extension to PTFE dispersions. A key point made in the book mentioned above is that up to 40% by volume of fillers are added to granular PTFE without complete loss of physical properties. Further claimed is that the impact of fillers added below 5 volume percent has no significant effect on PTFE properties. Typical fillers include glass beads or fiberglass that improve stiffness and creep resistance. Carbon filler is used for thermal conductivity and electrical conductivity enhancement. Carbon fiber fillers are utilized for more reinforcement and increasing of dimensional stability. Graphite fillers are added for achieving a lower coefficient of friction and improved wear resistance. Fillers such as bronze have been found to reduce deformation under load and raises thermal and electrical conductivity. Calcium fluoride can replace glass with better chemical resistance and molybdenum disulfide can be Introduced in order to increase hardness. Finally this reference book mentions that alumina and mica particles can be used as fillers that is still widely different from the type of additives disclosed in the present invention.

This reference book discusses the platelet structure of mica and how the platelets align with flow. It proceeds to mention that the physical properties of PTFE/mica compounds are "severely lowered" and notes that for fine powder PTFE based compounds, fillers are added to a much lesser extent than the granular PTFE materials. It claims that there are usually only three objectives of blending fillers or pigments into fine powder PTFE. These include coloration, increasing electrical conductivity and increasing abrasion resistance. The present invention does increase abrasion resistance and improve electrostatic dissipation but it also unexpectedly improves mechanical properties, the ability to process materials at thinner wall dimensions, and improves heat shrink capability of PTFE.

The reference book entitled "Fluoroplastics, Volume 2, Melt Processible Fluoropolymers" summarizes all key aspects of fluoropolymers processed via melt extrusion. Our inventive concept for FEP is not contained in this comprehensive treatise.

BRIEF DESCRIPTION OF THE DRAWINGS

While the invention is particularly pointed out and distinctly claimed in the concluding portions herein, a preferred embodiment is set forth in the following detailed description which may be best understood when read in connection with the accompanying drawings, in which:

FIG. 1 is a chart displaying mechanical and other properties of various wall thicknesses for PTFE tubing produced in accordance with the present invention;

FIG. 2 is a schematic illustration of a portion of the process of the present invention;

FIG. 3 is an illustration of the desired state of PTFE/Clay intercalation and exfoliation. Note the possibility of incorporating Fluorine functionality into the basic clay structure; and FIG. 4 is an illustration characteristic of our current practice of PTFE composite technology that tracks the distance between smectite clay platelets through each major step of the PTFE paste extrusion process. These spacings were measured via x-ray diffraction.

DETAILED DESCRIPTION OF THE PREFERRED EMBODIMENTS

The present invention is particularly usable for facilitating extrusion of material in paste form. The paste preferably consists of a fine PTFE powder that is initially mixed with a lubricant. These lubricants can be chosen from many different materials such as a range of hydrocarbon fluids that include Naphtha and ISOPAR solvents, along with liquids such as mineral spirits, and/or isopropyl alcohol. The lubricated powder paste mixture is then mixed with intercalated clay particles and compression molded into a preform. These preforms can be of any shape, however, commonly a hollow or solid cylinder is the chosen shape. The preform is placed into a ram extruder where it is extruded under pressure through a die and mandrel, a slit die, or other type of die configuration in order to provide the desired profile and extruded part dimension and configuration. The temperature of the material in the extrusion barrel and in the die area is normally chosen to be between room temperature and 300 degrees Fahrenheit.

A key aspect of the present invention is the choice of nanoparticles chosen to make the PTFE composite. The most common commercially available nanoparticles are available from Nanocor and Southern Clay companies and they are marketed as Nanomers and Laponite, respectively. Nanomers are based on montmorillonite natural clay and Laponites are synthetic hectorites. We have contemplated the use of all clay minerals classified as smectites and related 2:1 layer minerals, clay minerals, Kaolinite and related minerals. The particular nanoparticles used in our investigation is known commercially as I30 Nanoner from Nanocor for the PTFE work and I28 Nanomer for the FEP composites. One aspect that distinguishes the various grades of the smectite-layered silicates is the surface treatment between the clay layers. This surface treatment serves two purposes, to expand or intercalate the silicate layers and to make the mineral surface more compatible with polymers.

Another key aspect of the present invention both for the PTFE ram extruded materials and for the FEP meet compounded materials is that the I28 and I30 surface treatments were NOT designed for fluoropolymers. What is particularly unique about our invention is that these surface treatments actually change chemically during processing. Carbonization and other chemical changes unexpectedly led to novel properties in our composites. One area that we have studied is using functionalized layered silicates with fluorine functionality on the clay surface. These materials are available commercially from Southern Clay Products as Laponite B. We refer you to the book titled "Chemistry of Figments and Fillers", by D. G. Hawthorne and D. H. Solomon, 1991, Krieger Publishing Company. This book lists many historical details of controlling surface treatments on minerals, intercalation, and other fine details of nanoparticles contemplated for this invention Thereafter, the extruded material is passed through a series of processing ovens. Normally, there are two to six or as many as twelve ovens. The first grouping, that includes one or more ovens, is set to a temperature that will flash the lubricant component from the PTFE extrudate. The material is thereafter passed through as many as four ovens or oven sections for the purpose of heating the extrudate above the crystalline melting point of the PTFE component for sintering thereof. The extrudate may also be heated to the crystalline melting point of PTFE, without exceeding it, in order to produce material that is not sintered or partially sintered, if so desired.

The present invention includes a novel process for forming a product with unexpected properties by utilizing a dual preform having a separate inner and outer sections joined together. Either section can be formed of a composite material and either section can be pure PTFE. This two-section configuration provides product and process advantages not otherwise anticipated heretofore. The single wall preform FTFE composite also provides unique properties versus virgin PTFE.

One of the important advantages of the present invention is in the specific details of the manner for mixing the components. The mixing of the lubricant such as naphtha and PTFE enables the ram extrusion process to be successful. The addition of nanoparticles to this typical process enables thinner wall extrusion to wall thicknesses less than 0.001 inches accompanied by improved mechanical properties. One of the key process variables is in the choice of the concentration of the filler particles. The naphtha penetrates the platelet fillers and effectively increases their spacing therebetween. Furthermore, the sintering oven burns and degrades the filler surface treatment for yielding a composite having unexpected high performance characteristics. Tubing produced under this process can effectively be used to make heat shrink tubing with a shrinkage ratio of 9:1. The enhanced properties of the final articles produced under this process have equaled or surpassed class VI medical approval. Most of the examples described herein relate to PTFE paste extrusion, but it is also possible to produce melt compounded materials with FEP that can be processed for the production of tubing for medical related purposes, layflat tubing for packaging in the semiconductor industry with improved electrostatic discharge characteristics, or for heat shrink tubing.

One of the primary applications of the process and products of the present invention is the effect of clay nanoparticles in PTFE paste extrusions for catheter tubing. One of the primary purposes of this design is to produce functional materials with wall thickness less than the current capability of approximately 0.001". The two-section configuration described herein provides a dual preform approach wherein a filled system is located on the outer portion of the tube and a neat PTFE on the inner section thereof or the opposite configuration or even a single composite preform depending on the desired properties in the final product.

It has been discovered that nanoparticles improve the modulus, and tensile strength of PTFE tubing with equal to lower coefficient of friction and equal burst pressure. The use of the dual preform approach has been found to be superior to the single wall approach. Also, loading with 3% Nanomer has been determined to be superior to 7% nanomer loading. Further, the intercalation of the nanoparticle clays is not affected by the time of the addition of the nanoparticles in the process, i.e. added in the naphtha or in the PTFE fine powder.

A ram/cat puller is used to pull the tubing through the processing stations. While holding cat speed and temperature constant, the ram speed may be varied to achieve certain desired dimensions. This process has been found to be usable without encountering pinhole problems often associated with the addition of fillers.

Process Variables that are Independent and Dependent

| Independent Variables | Dependent Variables |
|---|---|
| Percentage Clay | Class VI Medical |
| Wall Thickness | Burst Pressure |
| Powder Age | Mechanical Properties |
| Powder Temperature | Pinholes |
| Dual Versus Single Preform | COF |
| Cat Speed | Etching |
| Barrel/Die Temperatures | Intercalation & Exfoliation |
| Clay addition point | Gamma Resistance |
| Clay Type | Sintering |
| Die/Mandrel Selection | Heat shrink ratio |

The addition of nanoparticles to PTFE has many advantages including lower paste extrusion pressures, reducing wall thicknesses without loss of mechanical properties, without the loss and in some cases improvement in lubricity as measured by coefficient of friction. Furthermore, significant mechanical properties have been improved and the ability to reduce wall thickness is a enhanced to a thickness of about 0.0007 inches.

During a series of trials using naphtha mixed with PTFE powder the aging time of naphtha with PTFE, aging temperature and nanoparticles added during or after aging were all varied in a controlled manner. It was determined that aging the powder with Naphtha 4 to 8 days prior to adding the Nanoparticles provides improved product. Additionally, aging at 24 hours at 100 degrees Fahrenheit with nanoparticles present is another optimum condition. Also, the 100 degree Fahrenheit 24 hour condition appears to give benefit to virgin PTFE as well. We have also demonstrated the utility of this invention when employing a mixture of lubricants, one specific example comprising a 90/10 mixture of naphtha/ISOPAR G hydrocarbon fluids.

Generally, the present invention includes a unique advancement in the fabrication and processing of fine powder poly(tetrafluoroethylene)(PTFE). The preferred application herein is making PTFE into tubing and rods for various purposes such as catheter liners, wire coatings, medical packaging, and many other products also. The preferred advancement of this invention is the addition of approximately 3% of one of several nanoparticles for PTFE paste extrusion. In this manner, a PTFE material is produced having as much as twice the modulus and twice the tensile strength of other known PTFE materials with the ability to extrude it into a thinner wall. Most prior art processes vary the properties of the final material with the addition of 5% or greater loading of fillers.

It has been discovered that when mixing 90% of virgin FEP material with, 10% of FEP containing 4% I30 Nanomer clay particles that a layflat tubing produced via melt extrusion exhibited accelerated discharge of electricity. This is commonly referred to in the industry as a material with enhanced electrostatic discharge characteristics.

The 10% component containing the 4% Nanomer can be compounded by typical melt compounding procedures such as twin-screw extrusion. In this case we found it necessary to minimize melt compounding temperatures for the best results. This FEP composite containing 4% Nanomer was then pellet blended with virgin FEP extrusion grade material that are available from Daikin, Dyneon, Dupont, and Asahi Glass. This blend was a 90/10 ratio by weight of virgin FEP to FEP composite. The FEP used to make the 4%.composite was based on a 22 melt flow index resin and the virgin FEP was based on a lower melt flow resin of about 3 more suitable for the layflat melt extrusion process.

We unexpectedly could lower the layflat melt processing temperatures of the virgin FEP material by over 100 degrees F. upon the addition of 10% FEP composite.

This process can make products from any base material but is particularly useful when working with paste extrusion of PTFE and melt extrusion of FEP. Many grades of FTFE can go into paste extrusion. Many fluoropolymers marketed as PTFE contain less than 1% of a comonomer for molecular weight and particle size control. A wide range of concentrations of the nanoparticles is useful in the present invention with 3% to 5% being preferred but possibly extending from 1 to 10%. This material is primarily useful for making a thin walled tubing for many applications but particularly advantageous for lubricious catheter material. Use of a 3% nanoparticles is particularly unique, especially because this concentration level can produce a doubling of the modulus and allows very thin wall thicknesses. These properties are shown particularly in the three-column table of data shown in FIG. 1. This chart and the other three figures all taken together show that control of mechanical and other properties is possible by varying the nanoparticles, particularly at lower concentration levels. Some aspects of the processing of the paste extrusions are important to carefully control in order to have a final product with the desired properties. with paste extrusions, a fine powder PTFE is used. There are a wide range of PTFE materials available of vastly different particle sizes or grades. The choice of grade of PTFE for a particular application is dictated by the reduction ratio. In paste extrusion, a lubricant is blended with the powdered PTFE. It is then placed into a compression mold to create a preform.

Thus, the first step in the paste extrusion procedure is to take the powder PTFE, mix it with a lubricant and let it sit for a period of time. Then it is pressed into a solid cylinder as a preliminary step to ultimately form a tube or rod. This cylinder is called a preform. The preform has an outside diameter of a particular dimension, and if it is a cylinder, there is a circle in the middle of the cylinder to define an annulus of material. If the hole in the cylinder is larger, then naturally a thinner walled cylinder is defined. This annular shape will be from approximately 0.5 inches to 10 inches in outside diameter, and the inner hole can be any of a wide range of sizes.

The wall thickness of the annular cylinder usually is initially very thick. But the tube or rod made from this annular cylinder after pushing it through a dye that tapers down can yield a very thin walled tubular or rod shaped member. As an example, consider a two-inch outside diameter preform that has a one-half inch diameter hollow diameter hole in it. The wall thickness will be 0.75 inches. Utilizing a ram extrusion process, the preform is rammed through a much smaller hole or annulus at very high pressure. An annulus is formed via a die/mandrel combination. In this example, the 0.75-inch wall thickness will be ramming through a diameter that may actually push the wall thickness down to a few thousandths of an inch. It can be heated during this ram extrusion process to enhance the flow of the material.

This process is often referred to as a solid-state extrusion. Heating it up to 200 degrees Centigrade is helpful in certain applications. The melting point of PTFE is approximately 340 degrees Centigrade, so this initial extrusion step does indeed occur well below the melting temperature of the PTFE material. It must be appreciated that whenever lubricant is mixed with the PTFE material, it helps it to extrude and form during ram extrusion. That material may be extruded at pressures anywhere from 1,000 to 75,000 pounds per square inch (psi). The ramming will push the material through a very small aperture. Thus we see that the paste extrusion process does include ramming of a preform of hardened paste through a predefined form. For these reasons this process can be referred to as paste extrusion, ram extrusion, or solid state extrusion.

In the solid-state extrusion it is often necessary to heat the material. Heating can be from a low value of above 30 degrees Centigrade, which is about room temperature. Heating to such a low temperature is an acceptable level because PTFE has two thermodynamic phase transitions at 19 and 30 degrees Centigrade, so the molecules start to become a more mobile above 30 degrees Centigrade.

It must be appreciated that when the powder is mixed with the lubricant before making the preform, the mix should be rolled below about 19 degrees Centigrade. This is necessary because if it is mixed above that first phase transition, fibrillation of the PTFE can occur, which will yield a low quality material for the final product. Once this preform is made, it is extruded through a smaller hole, and it comes out as a tube rod, or other shapes. After it comes out, it still contains lubricant. The defined reduction ratio for this extrusion as the ratio of the cross sectional area of your initial preform to the square cross-sectional area of the final tube, rod or other shape. This ratio can be as high as 10000 or more but is usually between 100 and 5,000. The grade of the PTEE is based on the reduction ratio of the process in the intended application. For higher reduction ratios, the molecular weight desired for the PTFE must be lower. This relationship is important because the lower molecular weight PTFE will extrude through the ramming extrusion aperture easier. In addition to controlling the molecular weight of PTFE to influence reduction ratio it is also known in the art that there are also methods to add low percentages of comonomers and also methods to produce engineered PTFE powder particles with dual chemical compositions and/or molecular weights to tailor the PTFE powder for particular applications.

It is important to appreciate that when mixing this lubricant with the PTFE powder before pressing of the preform, there is a wide range of lubricants that can be chosen, and those different lubricants have many different attributes. Some will give higher or lower pressure characteristics whereas some give more strength. These lubricants can be many materials such as naphtha or Isopars (a trade name of ExxonMobil) such as Isopar E, G, M or others. This first group of lubricants is broadly referred to as hydrocarbon fluids. Many of the lubricants are petroleum based such as naphtha or isopropyl alcohol. Naphtha is one of the most commonly used lubricants. The lubricant can be chosen from a wide variety of petroleum-based materials that enable one to do paste, solid state, or ram extrusion.

In accordance with one embodiment of the present invention, the preform is pressed in dual sections and is called a "dual preform". The present invention can also be practiced with a preform made of one single homogeneous material. However, the dual preform comprises two hollow concentric annular cylinders with one smaller than the other such that the smaller one can be placed within the innermost hole of the large one. Thus an inner and outer preform sections are defined. In one embodiment, the inner section will be completely made from virgin PTFE and the outer section is made from PTFE with the nanoparticles mixed therein. In this manner, the final preform is pressed with nanocomposite PTFE on the outside section and straight PTFE on the inner diameter section. These two pieces are then pressed together. That is, they are compression molded into one preform that still has all of the same size physical dimensions of the homogenous preform, except the actual nanocomposite portion is only on the outside diameter of the preform. In this manner the materials used by the medical or other equipment manufacturer to flow down the central aperture in the final tubes formed by this process will only contact virgin PTFE material similar to the material used heretofore in such medical tubing. This is a primary advantage of the double section preform design to allow it to be more widely accepted by the medical community since the material passing through the tubing will only contact material whose characteristics are well known already.

It has been determined that the final products have better properties and better extrusion characteristics with the dual preform than was possible with the single preform. However, There will be cases where the PTFE composite on the inner layer can provide improved surfaces in catheters in which stents and balloons can slide more easily.

In summary, the present invention uses approximately three percent nanoparticles in PTFE preforms for achieving enhanced properties in the final product. It is possible to extrude to thinner wall dimension under this process without significant loss of mechanical properties. Mixing of the lubricant with the PTFE powder in a controlled manner has achieved important characteristics also. The normal way of mixing a lubricant with the PTFE powder is to mix it in jars and roll these jars for up to 24 hours. It is necessary to keep it cold so that the resin does not fibrillate. After rolling for 24 hours, it can age for up to another 24 hours without further rolling and then the preform is pressed. However, for these composite blends, the timing of mixing and aging is much more critical. These nanoparticles, which are very absorbent, will tend to absorb the lubricant to the point where the lubricant will not sufficiently lubricate the PTFE anymore.

To overcome this problem it is necessary to mix the normal amount of lubricant with the PTFE and then to let it sit for four to eight days before adding the nanoparticle. Immediately prior to further processing the nanoparticles were added. This last minute adding of the nanoparticles allows the PTFE to be more adequately lubricated without competition from the nanoparticles. Another important aspect of the process according to the present invention is the oven design. The first oven usually is called the flash oven because it is used primarily to flash off the lubricant because it is not desirable to have any lubricant in the final product. Lubricant is flashed off at about 500 degrees Fahrenheit. If the initial oven were much greater than this temperature, the formed part might catch on fire because of the flammable petroleum based lubricant. There can be as many flash ovens as deemed necessary such as one, two, three, or more. These ovens preferably have cylindrical holes in them.

In the next oven zone the material then passes through the sintering oven areas. For sintering one must heat the material above 340 degrees Centigrade, which is the melting point of PTFE. It must be appreciated that with almost every other material, you would melt it, and extrude it, and cool it into its solid final shape. With this material the melting occurs in the sintering oven basically, but it is not a typical melt because PTFE when it melts, it is not melt processible, it just softens. So you are sintering it above its melting point, then you roll it up on a roll, or you cut it into pieces. The temperature will range in the sintering oven could be anywhere from 650 degrees Fahrenheit to 1200 degrees Fahrenheit A typical process for this material might include anywhere from two to ten different oven zones between the extruder and the cat puller which is responsible for pulling this tube, and two to ten separate temperature controlled zones, which are called separate ovens. They might not be actually physically separate ovens but would need to have different and separately controllable temperature zones.

The sintering step melts the material such that it becomes more homogeneous with less voids and less defects in the wall of the tube. Also, the orientation of the material can be varied based upon the temperature of the ovens and the stress placed on the tube. Also, as more strain is put on the tube with the cat puller during processing, more orientation will be put into the molecular structure of the material. This orientation is advantageous in some applications and disadvantageous in other applications. Orientation of the material distinctly affects the material properties.

For example, if the cat puller is moving slow and the oven temperatures are somewhat hotter, the orientation in the material is less pronounced. If the current application is for the making of pressure tubing then minimizing orientation is a preferred aspect of the process. Also minimizing orientation is useful in other applications such as where one might need PTFE material with higher chemical resistance, or higher hoop strength, or improved tubing burst strength. One can minimize molecular orientation of the PTFE material by choosing the correct processing parameters such as the amount of stress put on the tube when drawn by the cat puller or carefully determining the temperatures of the sintering ovens. These processing conditions that determine the physical ways that the material is melted and cooled can be adjusted to yield different amounts of orientation for achieving different properties for different applications.

For FEP, a fluorinated ethylene propylene copolymer, that exhibits a melting point of approximately 270 degrees C. and is a copolymer of PTFE with hexafluoropropylene we have also demonstrated one aspect of oar invention for melt processable fluoropolymers.

while particular embodiments of this invention have been shown in the drawings and described above, it will be apparent, that many changes may be made in the form, arrangement and positioning of the various elements of the combination. In consideration thereof it should be understood that preferred embodiments of this invention disclosed herein are intended to be illustrative only and not intended to limit the scope of the invention.

What is claimed is:

1. A process for forming a part comprising:
   A. providing a fluoropolymer material;
   B. adding a lubricant to the fluoropolymer material to form a mixture therewith;
   C. adding nanoparticles to the mixture at a level of 1% to 10% by weight to form a nanoparticle reinforced fluoropolymer;
   D. molding of the nanoparticle reinforced fluoropolymer into a preform shape; and
   E. extruding of the preform shape into the desired final shape of the part.

2. A process as defined in claim 1 wherein the mixture formed by adding lubricant to the fluoropolymer material is in the form of a fluoropolymer paste.

3. A process as defined in claim 1 wherein providing of a fluoropolymer material comprises providing of a fluoropolymer in powder form.

4. A process as defined in claim 1 wherein said extruding of the preform shape into the desired final shape of the part comprises ram extrusion.

5. The process as defined in claim 4 wherein said ram extrusion is performed at a processing pressure of approximately 1,000 to 75,000 pounds per square inch.

6. A process as defined in claim 1 wherein said adding a lubricant to the fluoropolymer material and said adding nanoparticles to the mixture is performed simultaneously.

7. The process as defined in claim 1 further comprising heating of the final part subsequent to extruding thereof.

8. The process as defined in claim 7 wherein said heating is of a sufficient temperature and time duration to flash the lubricant from the extruded final part.

9. The process as defined in claim 7 wherein said heating is performed in several individual stages at different temperature levels.

10. The process as defined in claim 7 wherein said heating is of a sufficient temperature and time duration for sintering of the extruded final part.

11. The process for forming a part as defined in claim 2 wherein the adding of the lubricant to the fluoropolymer paste is performed at a concentration level of 10% to 40% by weight.

12. The process for forming a part as defined in claim 2 further comprising rolling of the mixture of fluoropolymer paste and lubricant prior to the adding of nanoparticles thereto.

13. The process for forming a part as defined in claim 2 further comprising rolling of the mixture of fluoropolymer paste and lubricant after said adding of nanoparticles thereto.

14. The process for forming a part as defined in claim 12 wherein said rolling of the mixture is performed for a time period of between 1 and 24 hours at a temperature of less than 65 degrees Fahrenheit.

15. The process for forming a part as defined in claim 2 further comprising aging of the mixture of fluoropolymer paste and lubricant prior to adding of nanoparticles thereto for a period of time between 4 and 8 days at a temperature of between 60 and 90 degrees Fahrenheit.

16. The process as defined in claim 1 further comprising heating of the preform shape to 200 degrees Centigrade during extruding thereof to facilitate extruding thereof.

17. The process as defined in claim 2 wherein the nanoparticles are added at about 3% by weight.

18. The process as defined in claim 1 wherein the preform shape is a rod and wherein the desired final shape of the part is a rod.

19. The process as defined in claim 18 wherein the outside diameter of the desired final shape is 0.005 inches to 5.000 inches.

20. The process as defined in claim 1 wherein the preform shape is tubular and wherein the desired final shape of the part is tubular.

21. The process as defined in claim 20 wherein the outside diameter of the desired final shape is 0.005 inches to 5.000 inches.

22. The process as defined in claim 20 wherein the wall thickness of the tubular shape of the final part is from 0.0007 inches to about 4.0000 inches.

23. The process as defined in claim 2 wherein said providing of the fluoropolymer paste comprises providing of a poly(tetrafluoroethylene) paste.

24. The process as defined in claim 2 wherein said providing of the fluoropolymer material includes a comonomer component therewith.

25. The process as defined in claim 2 wherein said adding nanoparticles comprises adding minerals from the smectite family.

26. The process as defined in claim 2 wherein said adding nanoparticles comprises adding montmorillonite clay.

27. The process as defined in claim 2 wherein said adding nanoparticles comprises adding synthetic hectorite.

28. The process as defined in claim 25 wherein the minerals in the smectite family includes clays that contain fluorine group components.

29. The process as defined in claim 25 wherein the minerals added from the smectite family are surface treated with a coating.

30. The process as defined in claim 29 further comprising sintering of the extrudate subsequent to extruding thereof to facilitate removal and degradation of the coating on the minerals therewithin.

31. The process as defined in claim 2 further comprising heating of the extrudate subsequent to extruding for sintering thereof.

32. The process as defined in claim 2 wherein said extruding of the preform shape includes stretching of the nanoparticle reinforced fluoropolymer paste to increase the alignment of the molecular orientation thereof.

33. The process as defined in claim 2 wherein said adding of a lubricant comprises adding of a hydrocarbon fluid thereto.

34. The process as defined in claim 2 wherein said adding of a lubricant comprises adding of naphtha thereto.

35. The process as defined in claim 2 wherein said adding of the lubricant is performed at a temperature of less than 65 degrees Fahrenheit.

36. The process as defined in claim 2 wherein the desired final shape of the part is a rod and wherein an outer layer of virgin PTFE is pressed thereon to form a dual layer rod configuration with a nanocomposite reinforced fluoropolymer rod core and a virgin PTFE outer layer bonded thereover to facilitate providing of a fusion rod used in the construction of catheters.

37. The process as defined in claim 2 wherein the final shape of the extruded part is a tube of nanoparticle reinforced fluoropolymer and wherein a rod of virgin PTFE is pressed within the center of the tube to form a rod-shaped configuration having a nanoparticle reinforced fluoropolymer outer skin and a virgin PTFE inner core bonded together by pressing to facilitate providing of a fusion rod.

38. The process as defined in claim 2 wherein the desired final shape of the part is a composite dual layer tube including an inner tubular layer and an outer tubular layer pressed thereover having an outside diameter between 0.005 inches and 5.000 inches.

39. The process as defined in claim 38 wherein the inner tubular layer is of a virgin PTFE and the outer tubular layer is of nanocomposite reinforced fluoropolymer.

40. The process as defined in claim 38 wherein the inner tubular layer is of a nanocomposite reinforced fluoropolymer and the outer tubular layer is of virgin FTFE.

41. The process as defined in claim 20 further comprising expanding of the tubing after extruding thereof to produce an expanded tubing which will be capable of shrinking back responsive to being exposed to heat and having enhanced shrink back capabilities.

42. A process for forming a part comprising:
    A. providing a melt-processible fluoropolymer material;
    B. adding nanoparticles to the material at a level of 1% to 10% by weight to form a fluoropolymer melt material which is nanoparticle reinforced and melt-processible; and
    C. extruding of the fluoropolymer melt material into a desired final shape of the part.

43. The process as defined in claim 42 wherein said extruding includes melting of the nanoparticle reinforced melt-processible fluoropolymer melt material.

44. The process as defined in claim 42 wherein the fluoropolymer melt material is selected from the group consisting of FEP, PVF, PVDF, PFA, THV, PCTFE and MFA.

45. The process as defined in claim 42 wherein adding nanoparticles is performed at approximately 4% by weight.

46. The process as defined in claim 42 wherein the nanoparticle reinforced melt-processible fluoropolymer is formed from a mixture of pellet blends of 90% virgin FEP and 10% reinforced fluoropolymer to facilitate lower extruding temperatures and enhancing melting characteristics thereof.

47. The process as defined in claim 42 wherein the desired final shape of the part is lay flat tubing with an outside diameter of 0.010 inches to 10.000 inches having enhanced electrostatic dissipative properties.

48. The process as defined in claim 42 wherein said adding nanoparticles includes adding of minerals of the smectite family.

49. The process as defined in claim 48 wherein said adding nanoparticles includes adding at least one montmorillonite clay.

50. The process as defined in claim 48 wherein said adding nanoparticles includes adding at least one synthetic hectorite.

51. The process as defined in claim 48 wherein the mineral of the smectite family includes a surface coating for enhancing dispersing thereof.

52. The process as defined in claim 48 wherein the minerals in the smectite family includes clays that contain fluorine group components.

53. The process as defined in claim 42 wherein said extruding of the nanoparticle reinforced melt-processible fluoropolymer melt material includes stretching thereof in a controlled manner to increase alignment of the molecular orientation thereof.

54. The process as defined in claim 42 wherein said extruding of the nanoparticle reinforced melt-processible fluoropolymer forms a rod as the desired final shape of the part having an outside diameter of between about 0.005 inches to about 5.000 inches.

55. The process as defined in claim 42 wherein said extruding of the nanoparticle reinforced melt-processible fluoropolymer forms a tube as the desired final shape of the part having an outside diameter of between about 0.005 inches to about 5.000 inches.

56. The process as defined in claim 42 wherein said extruding of the fluoropolymer melt material forms a lay flat tubing having an outside diameter of between about 0.010 inches to about 10.000 inches with enhanced electrostatic dissipative properties.

\* \* \* \* \*

UNITED STATES PATENT AND TRADEMARK OFFICE
CERTIFICATE OF CORRECTION

PATENT NO. : 6,863,852 B1
DATED : March 8, 2005
INVENTOR(S) : Robert L. Ballard and Eric R. George It is certified that error appears in the above-identified patent and that said Letters Patent is hereby corrected as shown below:

Column 14,
Line 22, "FTFE" should read -- PTFE --.

Signed and Sealed this

Sixteenth Day of August, 2005

JON W. DUDAS
*Director of the United States Patent and Trademark Office*